(12) United States Patent  
Trieu et al.

(10) Patent No.: US 9,138,209 B2  
(45) Date of Patent: Sep. 22, 2015

(54) ANNULUS REPAIR SYSTEM

(75) Inventors: Hai H. Trieu, Cordova, TN (US);  
Lehmann K. Li, Milford, CT (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1521 days.

(21) Appl. No.: 12/358,384

(22) Filed: Jan. 23, 2009

(65) Prior Publication Data

US 2010/0191295 A1 Jul. 29, 2010

(51) Int. Cl.
*A61F 2/44* (2006.01)
*A61B 17/56* (2006.01)
*A61B 17/00* (2006.01)
*A61F 2/46* (2006.01)
*A61B 17/04* (2006.01)
*A61F 2/30* (2006.01)

(52) U.S. Cl.
CPC ............ *A61B 17/0057* (2013.01); *A61F 2/442* (2013.01); *A61F 2/4611* (2013.01); *A61B 17/0401* (2013.01); *A61B 17/0487* (2013.01); *A61B 2017/0061* (2013.01); *A61B 2017/00588* (2013.01); *A61B 2017/00606* (2013.01); *A61B 2017/00623* (2013.01); *A61B 2017/00659* (2013.01); *A61B 2017/00867* (2013.01); *A61B 2017/0404* (2013.01); *A61B 2017/0409* (2013.01); *A61B 2017/0417* (2013.01); *A61B 2017/0496* (2013.01); *A61F 2002/30092* (2013.01); *A61F 2002/30293* (2013.01); *A61F 2002/30461* (2013.01); *A61F 2002/30462* (2013.01); *A61F 2002/4435* (2013.01); *A61F 2002/4627* (2013.01); *A61F 2210/0014* (2013.01); *A61F 2220/0075* (2013.01); *A61F 2230/0091* (2013.01); *A61F 2310/00017* (2013.01); *A61F 2310/00023* (2013.01); *A61F 2310/00976* (2013.01)

(58) Field of Classification Search
USPC .................. 606/86 R, 151, 153, 232–233; 623/17.11, 17.16
See application file for complete search history.

(56) References Cited

U.S. PATENT DOCUMENTS

| | | | |
|---|---|---|---|
| 7,081,120 B2 * | 7/2006 | Li et al. | 606/99 |
| 7,273,497 B2 | 9/2007 | Ferree | |
| 2003/0078579 A1 * | 4/2003 | Ferree | 606/53 |
| 2004/0002763 A1 * | 1/2004 | Phillips et al. | 623/17.16 |
| 2006/0247665 A1 | 11/2006 | Ferree | |
| 2007/0198021 A1 * | 8/2007 | Wales | 606/86 |

FOREIGN PATENT DOCUMENTS

| | | | | |
|---|---|---|---|---|
| CA | 2426138 | * | 8/2002 | A61F 2/44 |
| WO | 2006119034 A2 | | 11/2006 | |

* cited by examiner

*Primary Examiner* — Nicholas Woodall  
*Assistant Examiner* — Larry E. Waggle, Jr.

(57) ABSTRACT

An annulus repair system is provided. This repair system may cover a hole or opening in the annulus or repair a defect or damage to the annulus. In one embodiment, the annulus repair system comprises a blocking component that covers a hole in the annulus, a stabilizing component that helps stabilize the blocking component and a suturing material that connects the two components together. In certain embodiments, the annulus repair system may further comprise a cannula for guiding the blocking component, the stabilizing component and at least a portion of the suturing material through body tissue and into the disc space. Methods for utilizing the annulus repair system of the present invention also are provided.

17 Claims, 7 Drawing Sheets

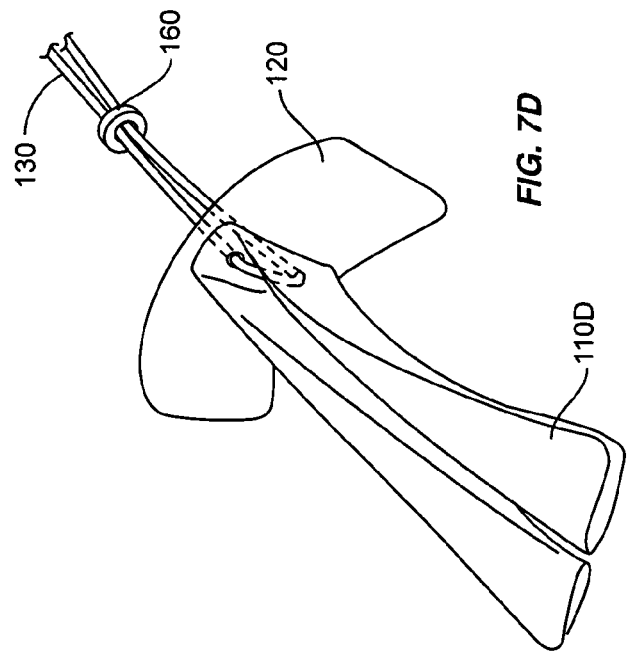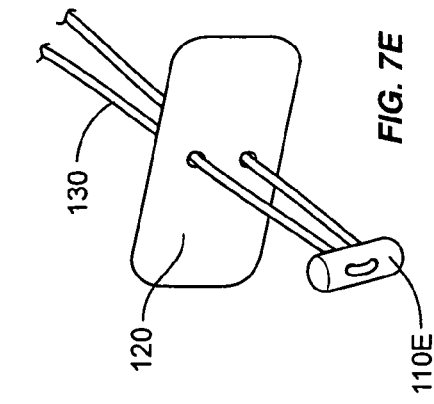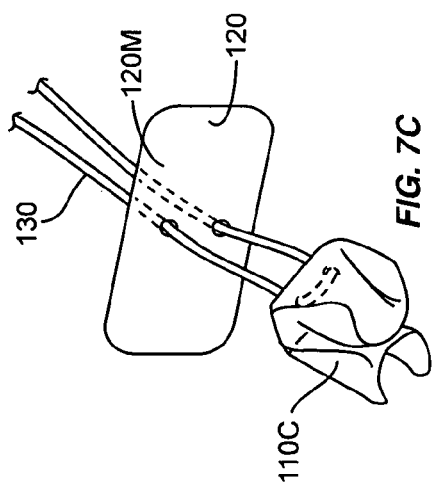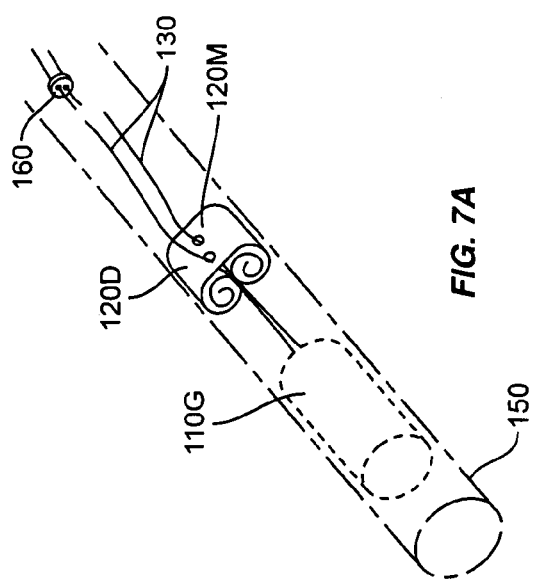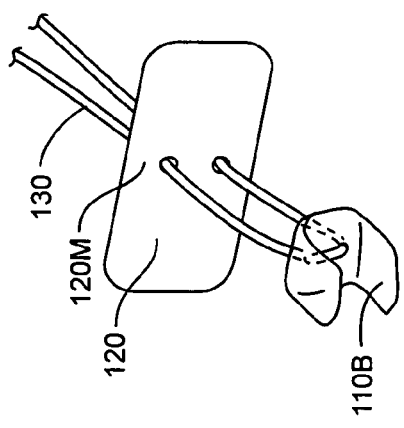
FIG. 7A
FIG. 7B
FIG. 7C
FIG. 7D
FIG. 7E

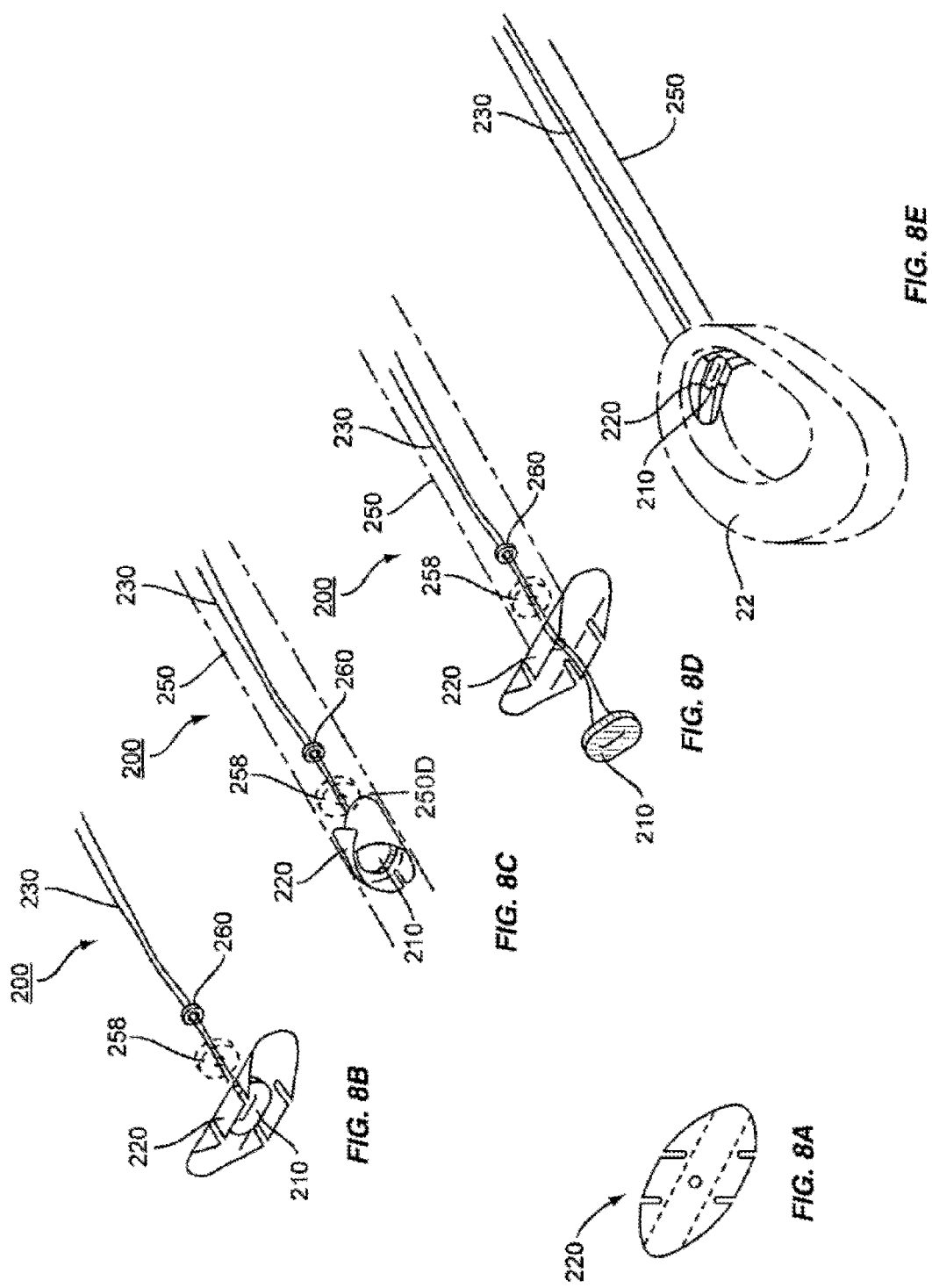

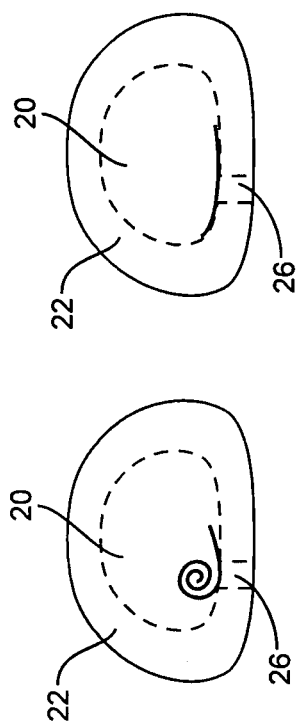
FIG. 10E
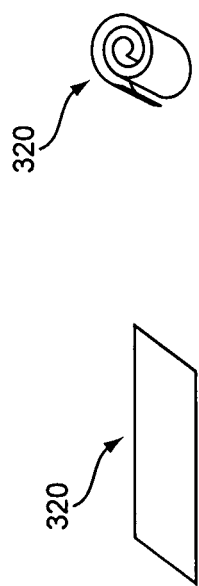
FIG. 9B
FIG. 10D
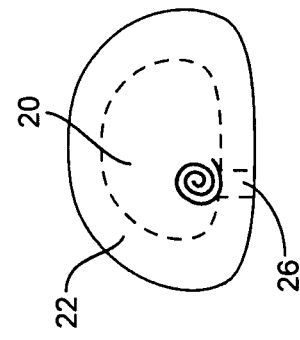
FIG. 9A
FIG. 10C
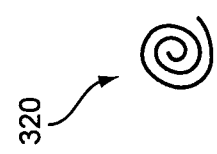
FIG. 10B
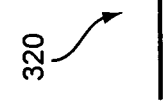
FIG. 10A

ANNULUS REPAIR SYSTEM

TECHNICAL FIELD

The invention relates to systems and methods for repairing damage to the annulus fibrosus.

BACKGROUND

The spinal column is a flexible chain of closely linked vertebral bodies. In a normal human spine there are seven cervical, twelve thoracic and five lumbar vertebral bodies. Below the lumbar vertebrae are the sacrum and coccyx. Each individual vertebra has an outer shell of hard, dense bone. Inside the vertebra is a honeycomb of cancellous bone containing red bone marrow. All of the red blood cells, and many of the white blood cells, are generated inside such cancellous bone, where the blood cells mature before being released into blood circulation.

The spinal disc serves as a cushion between the vertebral bodies so as to permit controlled motion. A healthy disc consists of three components: a gelatinous inner core called the nucleus pulposus; a series of overlapping and laminated plies of tough fibrous rings called the annulus fibrosus (or "annulus"); and two (i.e., superior and inferior) thin cartilage layers, connecting the disc to the thin cortical bone of the adjacent vertebral bodies, called the end plates.

The spinal disc may be displaced or damaged due to trauma or disease, such as a herniation or degenerative disc disease. A herniated disc may bulge out and compress itself onto a nerve, resulting in lower leg pain, loss of muscle control or paralysis. To treat a herniated disc, the offending nucleus portion is generally removed surgically.

Disc degeneration gradually reduces disc height, forcing the annulus to buckle, tear or separate radially or circumferentially, and causing persistent and disabling back pain. Degenerative disc disease is generally treated by surgically removing the nucleus and fusing the adjacent vertebral bodies so as to stabilize the joint. In either case, whether removing some or all of the nucleus, these procedures ultimately place greater stress on adjacent discs to compensate for the lack of motion, which may in turn cause premature degeneration of those adjacent discs.

It has been recognized that it may be possible to replace the excised nucleus with a prosthetic implant, whereby to restore the spinal disc to its original configuration and function. Unfortunately, such implants, sometimes referred to as a prosthetic nucleus, tend to suffer from one or more deficiencies.

One deficiency of current prosthetic nuclei is that the annulus is further weakened by either large or multiple cut-outs which are required in order to insert the prosthetic nucleus into the interior of the spinal disc. Additionally, any flaps or cut-outs of the annulus are not easily repaired.

Modern trends in surgery include the restoration of bodily function and form (i.e., the repair) of anatomical structures through the use of minimally invasive surgical techniques. The ability to surgically repair damaged tissues or joints, creating as few and as small incisions as possible, generally produces less trauma, less pain and better clinical outcomes for the patient.

Accordingly, there is a need for improved systems and techniques for repairing damage to the annulus, particularly when a small incision is made in the annulus for the insertion of a prosthetic disc.

SUMMARY

An annulus repair system is provided. This repair system may cover a hole or opening in the annulus or repair a defect or damage to the annulus. In one embodiment, the annulus repair system comprises a blocking component that covers a hole in the annulus, a stabilizing component that helps stabilize the blocking component and a suturing material that connects the two components together. In certain embodiments, the annulus repair system may further comprise a cannula for guiding the blocking component, the stabilizing component and at least a portion of the suturing material through body tissue and into the disc space.

In some embodiment, the annulus repair system further comprises a locking component that locks the blocking component, the stabilizing component and at least a portion of the suturing material together such that the blocking component covers the hole in the annulus. In certain embodiments of the annulus repair system of the present invention, one or both of the blocking component and the stabilizing component can be reduced in size to fit inside and slide along the cannula. In such embodiments, such components can be reduced in size by rolling them up to fit inside and slide along the cannula. Further, after such components have been deployed from the cannula into disc space, the one or both of the blocking component and the stabilizing component take on their final and intended shape such that the blocking component can cover the hole in the annulus. To help in this task, in certain embodiments of the annulus repair system of the present invention, at least one of the blocking component and the stabilizing component is made of a shape memory material, which can be for example a Nickel Titanium alloy. In certain embodiments of the annulus repair system of the present invention, the stabilizing component is a plug that can fit inside the cannula without being reduced in size.

In certain embodiments of the present invention, the annulus repair system comprises two components that are tethered together by a relatively thin length of material and work together to cover a hole or opening in the annulus or to repair a defect in or damage to the annulus. In such embodiments, the relatively thin length of material may be a suturing material for keeping the two components tethered together and pulling them taught such that at least one of two components covers the hole in the annulus.

Methods for utilizing the annulus repair system of the present invention also are provided. The method comprises the steps of providing a cannula, providing suturing material, providing two components that are tethered together by the suturing material, reducing the two components in size to the extent necessary so that they fit inside and slide along the cannula, placing the two components and at least a part of the suturing material into the cannula, positioning the cannula so that a distal end has been inserted through the hole in the annulus so that the distal end of the cannula has entered disc space on the interior of the annulus, moving the two components and at least the part of the suturing material through cannula so that the two components exit the distal end of the cannula and enter the disc space, and using the suturing material to pull the two components taught so that at least one of the two components covers the hole in the annulus.

In certain methods of annulus repair system according to the present invention, after the step of pulling the two components taught, the method further comprises placing a locking component into the cannula to lock and maintain the two components in place over the hole in the annulus. In some embodiments of annulus repair according to the present invention, after the step of placing the locking component in place, the method further comprises removing a part of the suturing material that is not necessary for covering the hole in the annulus and removing the cannula from the body.

Additional aspects and features of the present disclosure will be apparent from the detailed description and claims as set forth below.

BRIEF DESCRIPTION OF THE DRAWINGS

FIG. 7A is an isometric view of the annulus repair system of the present invention, and particularly illustrating a generic stabilizing element 110G.

FIG. 7B is an isometric view of a certain stabilizing element according to the present invention.

FIG. 7C is an isometric view of a certain stabilizing element according to the present invention.

FIG. 7D is an isometric view of a certain stabilizing element according to the present invention.

FIG. 7E is an isometric view of a certain stabilizing element according to the present invention.

FIG. 8A is an isometric view of a blocking component according to the present invention.

FIG. 8B is an isometric view of an annulus repair system according to the present invention.

FIG. 8C is an isometric view of the annulus repair system of FIG. 8B after it is inserted in a cannula.

FIG. 8D is an isometric view of the annulus repair system of FIG. 8B, and a distal plug and blocking component are deployed.

FIG. 8E is an isometric view of the annulus repair system of FIG. 8B in cooperation with an annulus.

FIG. 9A is an isometric view of a blocking component according to the present invention.

FIG. 9B is an isometric view of the blocking component of FIG. 9A after it has been reduced in size.

FIG. 10A is a cross-sectional view of the blocking component of FIG. 9A.

FIG. 10B is a cross-sectional view of the blocking component of FIG. 9B.

FIG. 10C is a cross-sectional view of the blocking component of FIG. 9A just after it has been inserted into the disc space.

FIG. 10D is a cross-sectional view of the blocking component of FIG. 9A as it begins to increase in size, or in this case, unroll.

FIG. 10E is a cross-sectional view of the blocking component of FIG. 9A after it has un-rolled.

DETAILED DESCRIPTION

Figure 1:
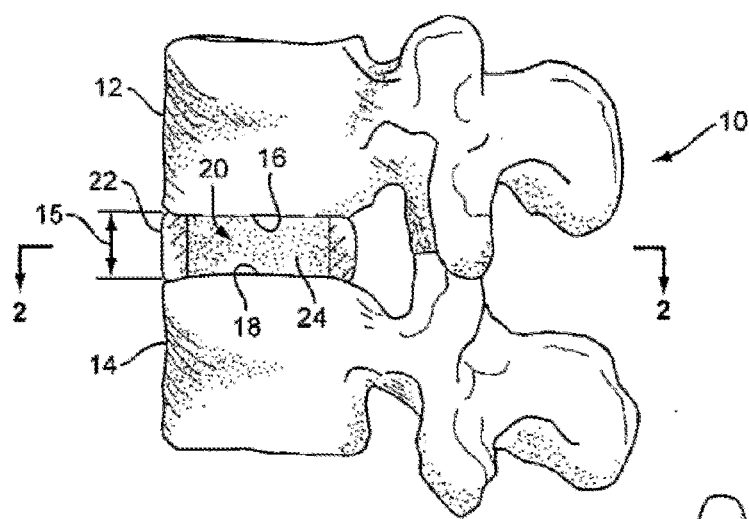
FIG. 1 is a cross-sectional lateral view of a section of spine.

For the purpose of promoting an understanding of the principles of the present disclosure, reference is made to the specific embodiments illustrated in the drawings, and specific language is used to describe the embodiments. It is nevertheless understood that no limitation of the scope of the present disclosure is intended. Any alterations and further modifications of the described embodiments, and any further applications of the principles of the present disclosure as described herein, are fully contemplated, as would occur to one skilled in the art to which the invention relates.

FIG. 1 shows a cross-sectional lateral view of a section of spine. The reference numeral 10 refers to a vertebral joint section or a motion segment of a vertebral column. The joint section 10 includes adjacent vertebral bodies 12 and 14. The vertebral bodies 12 and 14 include endplates 16 and 18, respectively. An intervertebral disc space 20 is located between the endplates 16 and 18, and an annulus fibrosus (or "annulus") 22 surrounds the disc space 20. In a healthy joint, the disc space 20 contains a nucleus pulposus 24 within the disc space 20, which helps maintain the distance between endplates 16 and 18, known as the disc height 15. Proper disc height 15 may vary for a particular patient, but medical experts understand how to determine a range of desired disc height 15. The nucleus pulposus 24 may degenerate with age, disease, or trauma, permitting the endplates 16 and 18, to move closer together.

Figure 2:
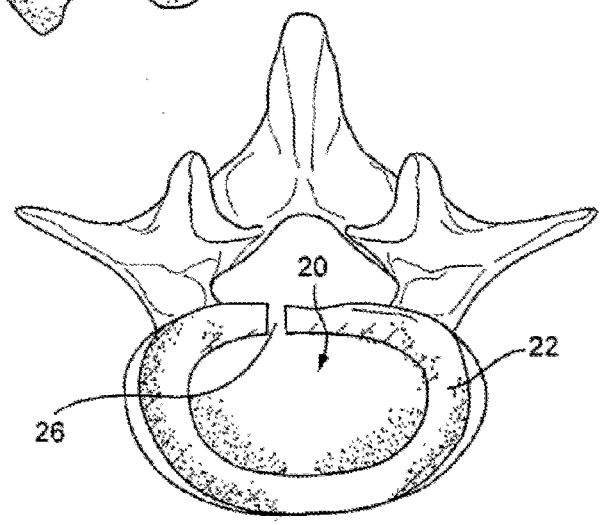
FIG. 2 is a cut-away elevation view of a specific layer of vertebrae.
Figure 3:
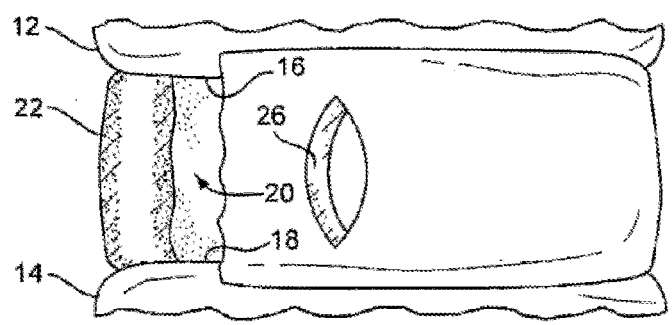
FIG. 3 is a cut-away, cross-sectional view of the layer over vertebrae of FIG. 2 from a posterior perspective.

Referring to FIGS. 2 and 3, an exemplary disc incision 26 is shown in the posterior wall of the annulus 22. FIG. 2 shows a cut-away elevation view of a specific layer of vertebrae, whereas FIG. 3 shows a cut-away, cross-sectional view of the same layer between vertebrae 12 and 14 from a posterior perspective. Disc incision 26 breaches the annulus fibrosus 22 to the disc space 20. As necessary, nucleus pulposus 24 may be removed from the disc space 20 in order to accommodate the insertion of a prosthesis. Illustratively or representatively shown empty in FIG. 2, the disc incision 26 is longitudinal in order to attempt to minimize trauma to the annulus 22. The anterior wall of the annulus 22 is shown, but the depicted procedure and device are not limited by the example. The particular surgical expert performing the procedure may choose to enter the annulus 22 from anterior, anterior oblique, posterior, posterior oblique, lateral, transforaminal, or any other approach deemed suitable with regard to other factors. Also, the particular surgical expert may choose to orient the disc incision 26 differently.

A dilator may be used to dilate the disc incision 26, making it large enough to deliver an implant to replace or augment the disc nucleus. The dilator may stretch the disc incision 26 temporarily and avoid tearing so that the disc incision 26 can return back to its un-dilated size after the dilator instrument is removed. Although some tearing or permanent stretching may occur, the dilation may be accomplished in a manner that allows the disc incision 26 to return to a size smaller than the dilated size after the implantation is complete.

Figure 6A:
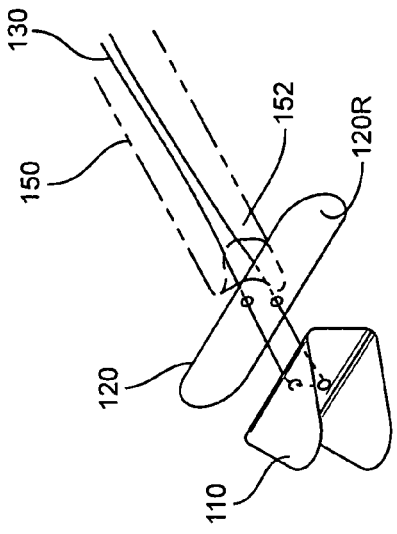
FIG. 6A is an isometric view of an annulus repair system according to the present invention.

The present invention addresses the problem of properly repairing a disc incision 26, a similar incision, hole, defect or other breach of the wall of the annulus 22. FIGS. 6A, 6B, 6C and 6D illustrate one embodiment of the annulus repair system 100 of the present invention in various isometric views of the system at various stages. Specifically, FIG. 6A shows the annulus repair system 100, which comprises a stabilizing component 110, a blocking component 120, suturing material 130, a tube or cannula 150 and a locking component 160 (shown in FIG. 6D). As shown in FIG. 6A, each of the components 110, 120 and 130 are contained in and confined to the cannula 150. As such, the cannula 150, with each of the other components contained therein, is designed to penetrate the annulus 22, through the hole or incision 26, for example.

Figure 4:
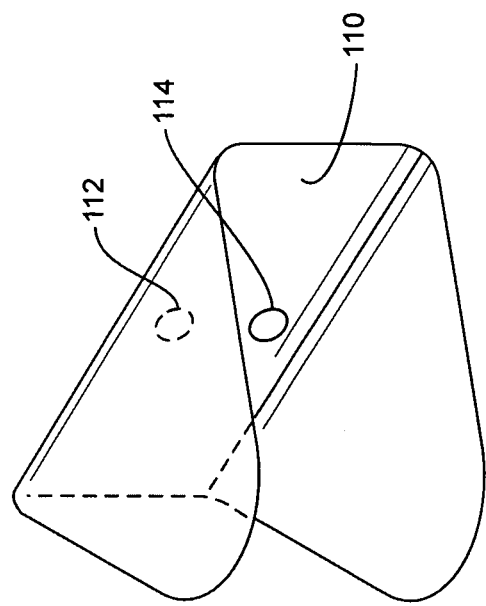
FIG. 4 is an isometric view of a stabilizing component according to the present invention.

FIG. 4 shows an isometric view of the stabilizing component 110. In one embodiment, stabilizing component 110 is made of a shape memory material (or shape memory alloy) such as Nickel Titanium ("NiTi") so that it can be reduced in overall size to fit in the cannula 150 and also take on its intended shape, as shown in FIG. 4. Other possible materials for the stabilizing component 110 are stainless steel, Titanium 64, polyetheretherketone ("PEEK"), polyethylene, polyurethane, polyester, polypropylene, silicone or combinations thereof. Additionally, as shown in FIG. 4, the stabilizing component 110 contains two holes 112 and 114 to accommodate the suturing material 130.

Figure 5:
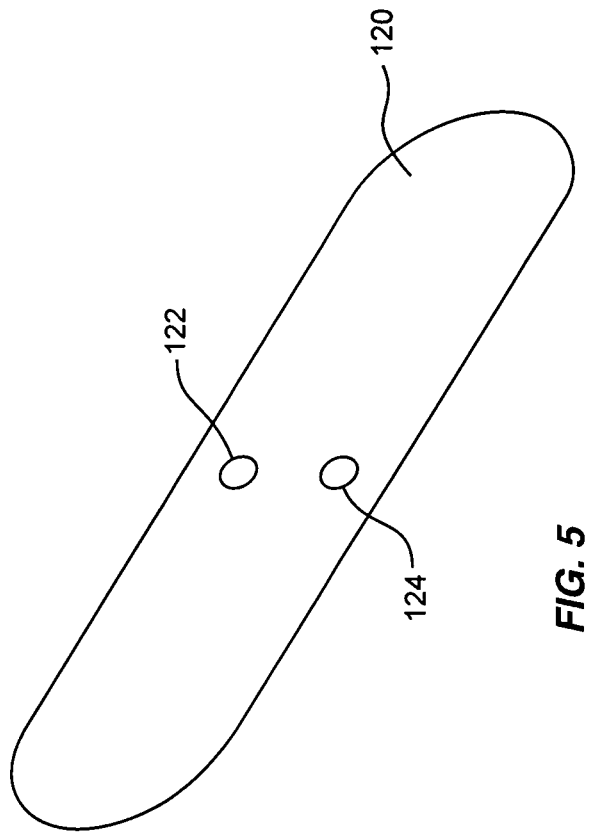
FIG. 5 is an isometric view of a blocking component according to the present invention.

FIG. 5 shows an isometric view of the blocking component 120. In one embodiment, blocking component 120 is made of a shape memory material such as Nickel Titanium ("NiTi") so that it can be reduced in overall size to fit in the cannula 150 and also take on its intended shape, as shown in FIG. 5. Other possible materials for the blocking component 120 are stainless steel, Titanium 64, polyetheretherketone ("PEEK"), polyethylene, polyurethane, silicone polyester, or combinations thereof. Additionally, the blocking component 120 may be covered with a fabric mesh, that optionally may be soaked with a growth factor or biological pharmaceutical agent to help the system 100 be incorporated into or assimilate with the annulus 22 and/or surrounding tissue. Further, as shown in FIG. 5, the blocking component 120 contains two holes 122 and 124 to accommodate the suturing material 130. Also note that the stabilizing component 110 and blocking component 110 may also be made somewhat flexible to properly mate and conform with the annulus 22.

As shown in FIG. 6A, a step in this embodiment of the annulus repair procedure is for all of the components 110, 120 and 130 to be inserted into the cannula 150. As shown, the stabilizing component 110 should be closer to the distal end 152 of the cannula 150, and the blocking component 120 should be closer to the proximal end 154 of the cannula 150. The components 110, 120 and 130 can be inserted into the cannula 150 at any time up until deployment of these components, i.e., before, during, or after insertion of the cannula 150 into the disc space 20. An instrument, such as a plunger, pushing rod or piston, for examples, can be utilized to move or push components 110, 120 and 130 through the cannula 150 from the proximal end 154 towards the distal end 152, and into the disc space 20.

Once the distal end 152 of the cannula 150 has passed through the hole 26 and entered the disc space 20 on the interior side of the annulus 22, the components of the annulus repair system 100 that perform the repairing can be deployed. FIG. 6B shows an isometric view of the annulus repair system 100 after the stabilizing component 110 is deployed. As shown in FIG. 6A, the stabilizing component 110 is reduced in size, or rolled up. As shown in FIG. 6B, the stabilizing component 110 is in its intended shape. The shape memory material helps the stabilizing component 110 accomplish this task. To illustrate the manner in which the stabilizing component 110 is rolled up in FIG. 6A, the top end 110T is labeled in both FIGS. 6A and 6B.

Figure 6C:
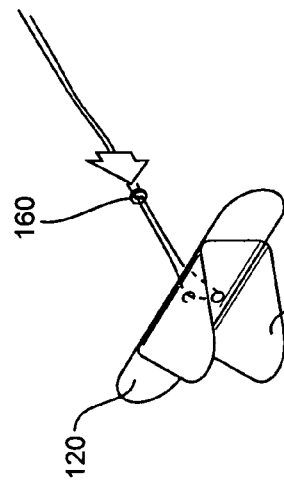
FIG. 6C is an isometric view of the annulus repair system of FIG. 6A after the stabilizing component and the blocking element are deployed.
Figure 6B:
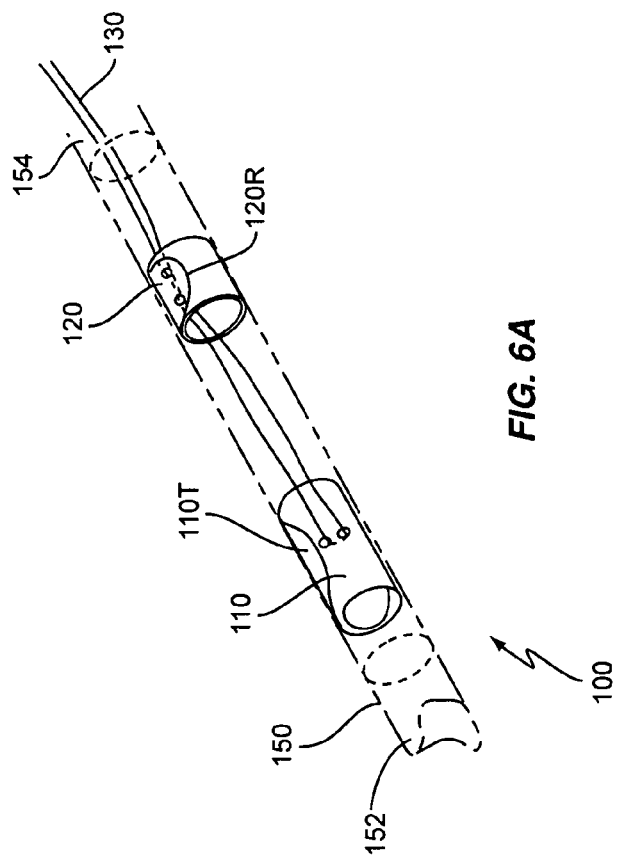
FIG. 6B is an isometric view of the annulus repair system of FIG. 6A after the stabilizing component is deployed.

The next stage of deployment is shown in FIG. 6C. Once the stabilizing component 110 is deployed, the blocking element 120 is deployed. As shown in FIG. 6C, the blocking element 120 is in its intended shape. The shape memory material helps the blocking element 120 accomplish this task. To illustrate the manner in which the blocking element 120 is rolled up to be placed in and slide along inside the cannula 150, the right hand side 120R of the blocking element 120 (as shown in the figures) is labeled in FIGS. 6A, 6B and 6C.

Figure 6D:
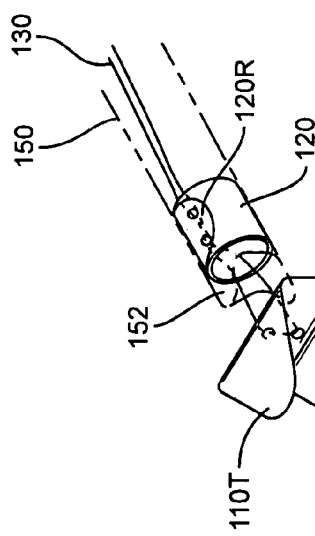
FIG. 6D is an isometric view of the annulus repair system of FIG. 6A after the stabilizing component and the blocking element are deployed, and the suturing material is activated or pulled in the direction away from the disc space.

To proceed from the state of the annulus repair system 100 as shown in FIG. 6C to that shown in FIG. 6D, the suturing material 130 is activated or pulled in the direction away from the disc space 20 and toward the proximal end of the cannula 150. Upon pulling the suturing material 130 in this direction, the suturing material 130 itself first pulls the stabilizing component 110 in the same direction back towards the annulus 22 until it contacts the blocking component 120 and then both the stabilizing component 110 and the blocking component 120 are pulled back against the annulus 22 to where the blocking component 120 covers the opening 26 in the annulus 22. After this is achieved, the locking component 160, which is situated outside the disc space 20, is moved in the direction toward the disc space 20 until it abuts the annulus 22. This locking component 160 is intended to lock components 110, 120 and 130 together and in place over the hole 26. At this point the remainder of the suturing material 130, that lying outside the disc space and located distally from the locking component 160 can be cut away and discarded. Note that the suturing material 130 can merely be a relatively thin length of material. Also note that the suturing material 130, which is used as a tether, can also be a wire or cable or the like. Suitable materials for the suturing material include, but are not limited to, polyester, polyethylene, polyetheretherketone ("PEEK"), Titanium, or stainless steel.

FIG. 7A shows another embodiment of the annulus repair system 100 of the present invention. Specifically, FIG. 7A shows an isometric view of the stabilizing element 110G, and specifically illustrating a generic stabilizing element 110G. In addition, FIG. 7A shows a blocking element 120D in a different "rolled-up" configuration than that shown in FIGS. 6A and 6B. As shown in FIG. 7A, blocking element 120D has a dual-roll configuration (as opposed to the single-roll configuration of FIGS. 6A and 6B) with each half in its own rolled-up configuration. This emphasizes that the manner in which the blocking component 110G or 110 or stabilizing component 120D or 120 is reduced in size so as to fit inside the cannula may vary. For illustrative purposes, the middle portion 120M of the blocking element 120D is labeled in FIGS. 7A, 7B and 7C.

Similarly, a line is drawn from the generic stabilizing element 110G of FIG. 7A to each of FIGS. 7B, 7C, 7D and 7E to demonstrate that the stabilizing element 110G may also take on different forms. FIG. 7B shows an isometric view of a stabilizing element 110B. Stabilizing element 110B differs from stabilizing element 110 in that its top and bottom portions, after deployment, are more rectangular-shaped than the more triangular-shaped top and bottom portions of stabilizing element 110.

FIG. 7C shows an isometric view of a stabilizing element 110C. Stabilizing element 110C differs from stabilizing element 110B in that it is turn 90 degrees and the wing portions (or sections that are perpendicular to the portion of the stabilizing elements with the holes for the suturing material 130) each have respective sides that are bent in towards each other.

Similarly, FIG. 7D shows an isometric view of a stabilizing element 110D. Stabilizing element 110D differs from stabilizing element 110C in that its respective wing portions are longer and each rotates ninety degrees as they extend away from the annulus 22. In addition, FIG. 7D shows another view of the locking component 160. Note that in addition to taking on different shapes or forms, each of the forms of stabilizing element 110B, 110C and 110D also may be reduced in size or rolled up in various shapes so as to fit inside the cannula 150.

FIG. 7E shows an isometric view of a stabilizing element 110E. Stabilizing element 110E differs from all the other stabilizing elements introduced thus far in that it is not composed of a sheet of material or is similar to the embodiments shown and described in previous figures. That is, as shown, stabilizing element 110E is a plug member 110. This plug member may be merely a component that stabilizes the blocking component 120 and is small enough to slide through the cannula 150. Stabilizing element 110E also may be, for example, a dehydrated sponge or other porous material capable of being soaked with a growth factor or other biologics to achieve certain biological functions. As described above, a growth factor may be used to help the system 100 be incorporated into or assimilate with the environment in which it is placed. Further, as shown, just as stabilizing element 110 has two holes 112 and 114 for attachment to the rest of the annulus repair system by means of the suturing material 130, each of the stabilizing components 110B, 110C, 110D and 110E each contain two similar holes to accomplish the same function. Note that more or less holes through a stabilizing component can be used to accomplish the same function.

FIGS. 8A, 8B, 8C, 8D and 8E show isometric views of another embodiment of an annulus repair system 200 of the present invention. FIG. 8A shows a blocking component 220 when it is initially cut or formed to match the desired shape. As above, blocking component 220 may be made of a shape memory material (or shape memory alloy) such as NiTi. Other possible materials for the blocking component 220 are stainless steel, Titanium 64, polyetheretherketone ("PEEK"), polyethylene, polyurethane, polyester, polypropylene, silicone or combinations thereof.

FIG. 8B shows the annulus repair system 200 prior to its insertion into a cannula. As shown, the blocking component 220 is flattened out prior to its being rolled up, or reduced in size for being able to fit inside and slide within a cannula. FIG. 8B also shows a distal plug 210 and a proximal plug 258. As described above, these plugs 210 and 258 may be, for example, a dehydrated sponge or other porous material capable of being soaked with a growth factor or other biologics to achieve certain biological functions. As will be shown and described, the distal plug 210 also is intended to act as a stabilizing component for the annulus repair system 200.

FIG. 8C shows an isometric view of the annulus repair system 200 after the blocking component 220 is rolled up and it, along with the distal plug 210, proximal plug 258, locking component 260 and suturing material 230 are inserted into the cannula 250. FIG. 8D shows an isometric view of the annulus repair system 200 after the distal end 250D of the cannula 250 has penetrated the disc space and distal plug 210 and blocking component 220 are deployed. As shown, the blocking component 220 has now taken on its final intended shape to cover up the hole 26 in the annulus 22. Again, as described previously, the blocking component 220 (as well as a typical stabilizing component) can take on various forms to accomplish the job of fully covering the hole 26. In addition, as described previously, each blocking component (including blocking component 220) may be reduced in size by various methods, and/or simply differently rolled-up forms.

FIG. 8E shows an isometric view of the annulus repair system 200 in cooperation with an annulus 22 and after the stabilizing component/distal plug 210 and blocking component 220 have been pulled taught against the desired location in the annulus 22 by the suturing material 230. FIG. 8E shows the system 200 and annulus 22 just prior to cutting off the slack of the suturing material 230 and removal of the cannula 250.

FIGS. 9A and 9B show isometric views of another embodiment of a blocking component 320, which itself comprises another embodiment of an annulus repair system according to the present invention. FIG. 9A shows a blocking component in its un-rolled state. Note that the blocking component 320 can be made of the same materials of the previously described blocking components 120 and 220. The blocking component 320 takes on the shape shown in FIG. 9A both before insertion into a disc space 20 and after deployment in the disc space 20. For insertion into the disc space 20, through an opening 26, the blocking component 320 is reduced in size, or rolled-up, as shown in FIG. 9B. After insertion, the blocking component 320 can revert back to the shape of FIG. 9A, and a shape memory material of which it can be composed, will help in this regard.

FIGS. 10A, 10B, 10C and 10D shows cross sectional views of how blocking component 320 is deployed in the disc space 20. FIG. 10A shows the cross-sectional view of the blocking component 320 itself. FIG. 10B shows the cross-sectional view of the blocking component 320 of FIG. 9B. FIG. 10C shows the cross-sectional view of the stage just after the reduced-in-size blocking component 320 has been inserted into the disc space through the opening 26 in the annulus 22. FIG. 10D shows the cross-sectional view of the blocking component 320 as it begins to increase in size, or in this case, unroll. Lastly, FIG. 10E shows the cross-sectional view of the blocking component 320 after it has un-rolled completely to take on the shape of FIG. 9A or 10A, except for any changes to geometry of the annulus 22 around the opening 26. Note that there is no cannula in theses Figures demonstrating how the blocking component 320 is installed.

Similarly, with any of the embodiments of the present invention, there are times when a cannula may not be necessary. Further, note that, with any embodiments of the present invention, the annulus repair system may be utilized to correct a defect in the annulus 22. In such a case, an opening 26 may be made in the annulus 22 near the defect and a blocking component may be used to not only fix the defect, but also cover the opening 26.

Figure 11:
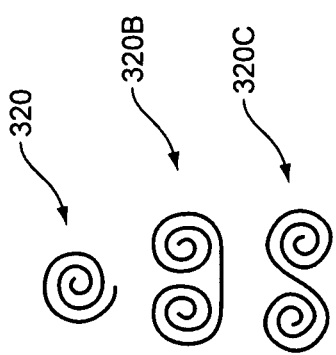
FIG. 11 depicts cross-sectional views of alternate embodiments of the blocking component of FIG. 9B or 10B.

FIG. 11 shows alternate embodiments of the blocking component 320 in the stage of FIG. 9B or 10B. In particular, FIG. 11 shows cross-sectional views of a single roll version 320, a double roll version 320B and an alternate double roll version 320C of blocking component 320.

Figure 12A:
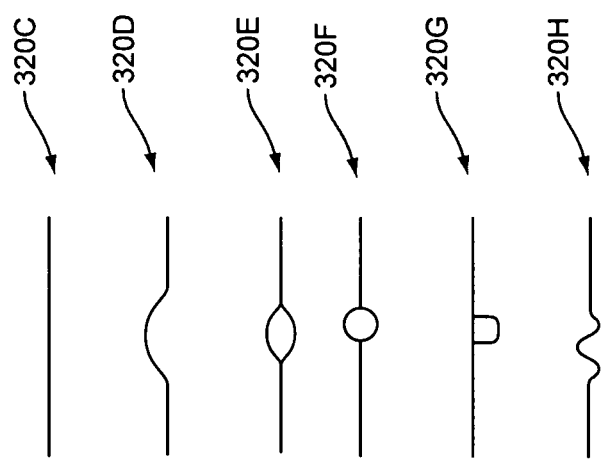
FIG. 12A depicts cross-sectional views of alternate embodiments of a blocking component according to the present invention.

FIG. 12A shows alternate embodiments of the blocking component 320 in the stage of FIG. 9A or 10A. In particular, FIG. 12A shows cross-sectional views of a flat sheet version 320, a version with a hump 320D, a version with a bump (a split in that location) 320E, a version with a rounded bump 320F, a version with a bulge 320G and a version with a wavy middle section 320H. Note that variations of the above are contemplated, and these are merely exemplary versions of blocking component 320.

Figure 13:
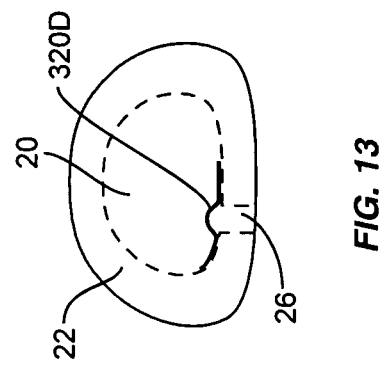
FIG. 13 is a cut-away elevation view of the blocking component of FIG. 12B in cooperation with an opening in an annulus.
Figure 12B:
FIG. 12B is an isometric view of a particular embodiment shown in FIG. 12A.

FIG. 12B shows an isometric view of version of blocking component 320 with a hump 320D. FIG. 13 shows one manner in which this version 320D can be deployed in cooperation with an opening 26 in an annulus 22. Again, note that the various embodiments of FIG. 12A (or any other annulus repair systems disclosed herein) can be used to correct a defect in the annulus 22. For example, the bulge of version 320G can be used to correct a defect, and the area on the blocking component 320G adjacent it can be used to cover the opening 26 that was created to insert the blocking component 320G.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed:

1. An annulus repair system comprising:
    a tubular blocking component extending between a first end and a second end, the blocking component having an interior facing surface defining a continuous passageway extending between the first and second ends and an exterior facing surface that covers a hole in an annulus from within a disc space, said exterior facing surface configured to contact an interior surface of the annulus;
    a stabilizing component having an interior facing surface and an exterior facing surface that helps stabilize the blocking component from within a disc space, the stabilizing component being configured for disposal within the passageway such that said exterior facing surface of said stabilizing component contacts the interior facing surface of the blocking component; and
    a suturing material that connects the two components together.

2. The annulus repair system of claim 1 further comprising:
    a cannula for guiding the blocking component, the stabilizing component and at least a portion of the suturing material through body tissue and into the disc space.

3. The annulus repair system of claim 2, wherein one or both of the blocking component and the stabilizing component can be reduced in size to fit inside and slide along the cannula.

4. The annulus repair system of claim 3, wherein one or both of the blocking component and the stabilizing component can be reduced in size by rolling them up to fit inside and slide along the cannula.

5. The annulus repair system of claim 3, wherein after the blocking component and the stabilizing component are deployed from the cannula into disc space, the one or both of the blocking component and the stabilizing component take on their final and intended shape such that the blocking component can cover the hole in the annulus.

6. The annulus repair system of claim 3, wherein at least one of the blocking component and the stabilizing component is made of a shape memory material.

7. The annulus repair system of claim 3, wherein at least one of the blocking component and the stabilizing component is made of Nickel Titanium alloy.

8. The annulus repair system of claim 3, wherein the stabilizing component is a plug that can fit inside the cannula without being reduced in size.

9. The annulus repair system of claim 1 further comprising:
    a locking component that locks the blocking component, the stabilizing component and at least a portion of the suturing material together such that the blocking component covers the hole in the annulus.

10. An annulus repair system comprising two components that are tethered together by a relatively thin length of material and work together to cover a hole in an annulus,
    wherein a first component of the two components extends between a first end and a second end and has an interior facing surface defining a continuous passageway extending between the first and second ends and an exterior facing surface that covers a hole in the annulus from within a disc space, said exterior facing surface configured to contact an interior surface of the annulus, and
    wherein a second component of the two components has an interior facing surface and an exterior facing surface that helps stabilize the first component from within a disc space, the second component being configured for disposal in the passageway such that said exterior facing surface of said second component contacts the interior facing surface of the first component.

11. The annulus repair system of claim 10 further comprising:
    a cannula for guiding the two components and at least a part of the relatively thin length of material through body tissue and into the disc space.

12. The annulus repair system of claim 11, wherein one or both of the two components can be reduced in size to fit inside and slide along the cannula.

13. The annulus repair system of claim 12, wherein one or both of the two components can be reduced in size by rolling them up to fit inside and slide along the cannula.

14. The annulus repair system of claim 10, wherein the relatively thin length of material is suturing material for keeping the two components tethered together and pulling them taut such that at least one of two components covers the hole in the annulus.

15. The annulus repair system of claim 10 further comprising:
    a locking component that locks the two components and at least a portion of the relatively thin length of material together such that at least one of two components covers the hole in the annulus.

16. The annulus repair system of claim 10, wherein at least one of the blocking component and the stabilizing component is made of a shape memory alloy.

17. The annulus repair system of claim 10, wherein at least one of the blocking component and the stabilizing component is made of Nickel Titanium alloy.

* * * * *